(12) United States Patent
D'Amelio et al.

(10) Patent No.: US 12,232,831 B2
(45) Date of Patent: Feb. 25, 2025

(54) ARTICULATED APPARATUS FOR SURGERY

(71) Applicant: Epica International, Inc., San Clemente, CA (US)

(72) Inventors: Frank D'Amelio, San Clemente, CA (US); Gianluca Parrini, Cascina (IT); Denis Mattia De Micheli, Navacchio di Cascina (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 652 days.

(21) Appl. No.: 16/428,660

(22) Filed: May 31, 2019

(65) Prior Publication Data

US 2019/0365487 A1 Dec. 5, 2019

Related U.S. Application Data

(60) Provisional application No. 62/680,448, filed on Jun. 4, 2018.

(51) Int. Cl.
*A61B 34/20* (2016.01)
*A61B 34/00* (2016.01)
*A61B 34/30* (2016.01)
*A61B 17/00* (2006.01)

(52) U.S. Cl.
CPC .............. *A61B 34/30* (2016.02); *A61B 34/20* (2016.02); *A61B 34/70* (2016.02); *A61B 17/00234* (2013.01); *A61B 2017/00473* (2013.01); *A61B 2034/301* (2016.02); *A61B 2034/305* (2016.02)

(58) Field of Classification Search
CPC ......... A61B 34/70; A61B 34/20; A61B 90/50; A61B 34/30; A61B 2034/305; A61B 17/00234; A61B 2090/067; A61B 2034/2059; A61B 2017/003; A61B 2017/00473; A61B 2034/301
See application file for complete search history.

(56) References Cited

U.S. PATENT DOCUMENTS

| | | | | |
|---|---|---|---|---|
| 4,930,494 | A | * 6/1990 | Takehana | A61B 1/0058 600/145 |
| 5,060,632 | A | * 10/1991 | Hibino | A61B 1/0005 600/109 |
| 2002/0062062 | A1 | * 5/2002 | Belson | A61B 1/0055 600/141 |

(Continued)

FOREIGN PATENT DOCUMENTS

WO  2018/005680 A1  1/2018

OTHER PUBLICATIONS

PCT International Search Report and Written Opinion issued Sep. 10, 2019 in corresponding PCT Application No. PCT/US2019/035329 filed Jun. 4, 2019 (EPICA International Inc.).

(Continued)

*Primary Examiner* — Stephen Holwerda
(74) *Attorney, Agent, or Firm* — STEPTOE LLP; Carl B. Wischhusen

(57) ABSTRACT

An apparatus for use in surgery is disclosed that includes an articulated instrument having a tip and at least one joint capable of bending, a controller for controlling the radius of bending of the instrument, and a sensor for calculating the amount of bending and the position of the tip of the articulated instrument.

6 Claims, 4 Drawing Sheets

(56) References Cited

U.S. PATENT DOCUMENTS

| | | | |
|---|---|---|---|
| 2002/0087048 A1 | 7/2002 | Brock et al. | |
| 2002/0120178 A1* | 8/2002 | Tartaglia | A61B 5/065 600/114 |
| 2003/0040737 A1* | 2/2003 | Merril | A61B 34/76 606/1 |
| 2003/0045778 A1* | 3/2003 | Ohline | A61B 1/31 600/114 |
| 2003/0208103 A1* | 11/2003 | Sonnenschein | A61B 90/06 600/117 |
| 2005/0020901 A1* | 1/2005 | Belson | G02B 23/2476 600/407 |
| 2005/0203382 A1* | 9/2005 | Govari | A61B 34/30 600/424 |
| 2005/0234293 A1* | 10/2005 | Yamamoto | A61B 90/57 600/102 |
| 2007/0060879 A1* | 3/2007 | Weitzner | A61M 25/1011 604/95.04 |
| 2007/0078301 A1* | 4/2007 | Kura | A61B 1/00042 600/106 |
| 2007/0173694 A1* | 7/2007 | Tsuji | A61B 1/0052 600/118 |
| 2008/0065110 A1* | 3/2008 | Duval | A61B 1/00149 606/130 |
| 2010/0069833 A1 | 3/2010 | Wenderow et al. | |
| 2010/0234856 A1* | 9/2010 | Stoianovici | A61B 34/70 606/130 |
| 2011/0319815 A1 | 12/2011 | Roelle et al. | |
| 2012/0143203 A1 | 6/2012 | Nishio et al. | |
| 2016/0235493 A1 | 8/2016 | LeBoeuf, II et al. | |
| 2017/0265840 A1 | 9/2017 | Bharat et al. | |
| 2017/0304012 A1 | 10/2017 | Tognaccini et al. | |
| 2017/0354468 A1 | 12/2017 | Johnson et al. | |

OTHER PUBLICATIONS

Bensignor et al. "Evaluation of the effect of a laparoscopic robotized needle holder on ergonomics and skills", Surgical Endoscopy, 2015, 9 pages. https://www.ncbi.nlm.nih.gov/pubmed/26017905. Retrieved from https://www.researchgate.net/publication/277410688_Evaluation_of_the_effect_of_a_laparoscopic_robotized_needle_holder_on_ergonomics_and_skills.

JAIMY-EN—Endocontrol Medical, Jun. 4, 2018, 9 pages. https://www.endocontrol-medical.com/en/jaimy-en/.

Extended European Search Report from EP application No. 19814620.1, mailed Feb. 8, 2022, 8 pages.

"Denavit-Hartenberg parameters", Wikipedia, Jan. 13, 2018, 10 pages, https://en.wikipedia.org/w/index.php?title=Denavit%E2%80%93Hartenberg_parameters&oldid=820119071.

Summons to attend oral proceedings, European Patent Application No. 19814620.1, Feb. 8, 2024, 6 pages.

* cited by examiner

ARTICULATED APPARATUS FOR SURGERY

CLAIM OF PRIORITY

This application claims priority from U.S. Provisional Application No. 62/680,448, filed on Jun. 4, 2018, which is incorporated by reference in its entirety.

BACKGROUND

Surgical instruments may often be rigid and inflexible. Even those instruments that are somewhat flexible often do not allow the surgeon to precisely know the position and orientation of the tip of the instrument with respect to another reference point. If there are various obstacles, such as arteries, organs, and bones between the incision and the target of the surgery, the surgeon may not be able to see the tip of the instrument and it may be difficult to perform the surgery accurately.

Figure 1:
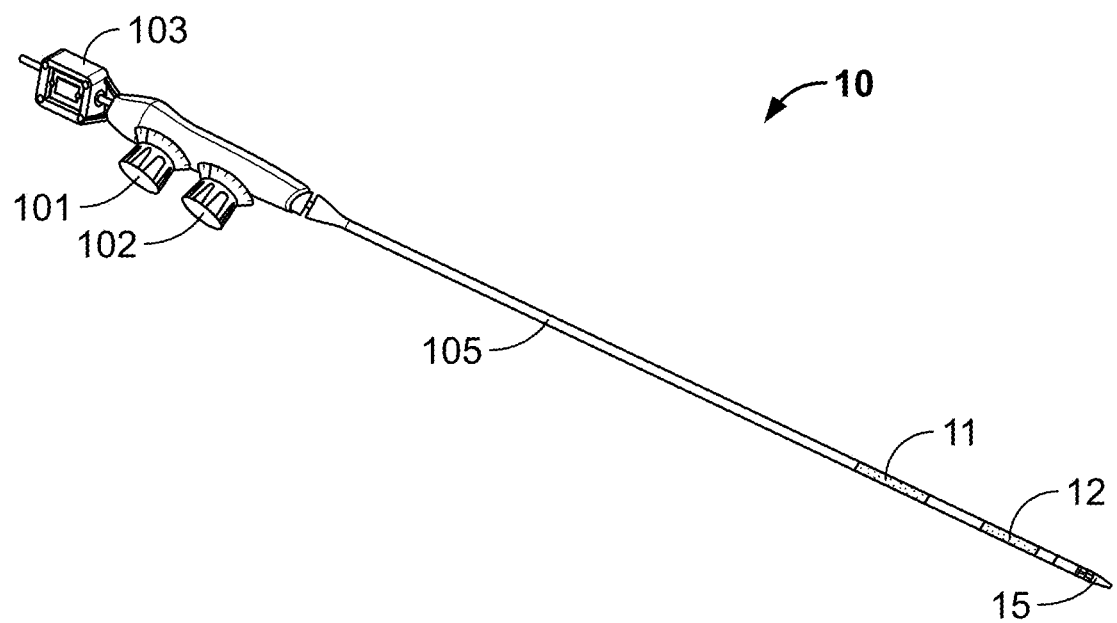
FIG. 1 is a schematic diagram of an articulated surgical instrument, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The inventors have developed an articulated surgical instrument that may be used to perform more accurate robotic surgery. This instrument has at least one joint that is capable of bending, a controller for controlling the radius of bending of the instrument, and a sensor for calculating the amount of bending and the position of the tip of the instrument. The instrument may also translate and/or rotate, and the sensor (or a second sensor) may calculate the amount of translation and/or rotation of the tip of the instrument. The articulated instrument may be inserted into a guide attached to a robotic arm, and the guide may include one or more sensors to track and calculate translation and/or rotation.

Reference is now made to FIG. 1, which is a schematic diagram of an articulated surgical instrument 10, according to an embodiment of the present invention. Surgical instrument 10 may be used for minimally invasive surgery such as laparoscopy. Surgical instrument 10 includes tip 15 and at least one joint, two of which are pictured in FIG. 1—first joint 11 and second joint 12. Joints 11 and 12 can independently bend, each bend having an angle (as shown in later figures). The bend angle of joints 11, 12, may be controlled using dials 101, 102, respectively. Dials 101, 102 may be sensorized and/or trackable so that the amount of dial rotation (and thus joint bend angle) may be kept track of. Surgical instrument 10 may move within sleeve 105. In some embodiments, tip 15 may translate (move forward and back) and/or may rotate within the sleeve, and both of these movements may be monitored by sensor 103, e.g., an optical sensor. If tip 15 does not translate or rotate, sensor 103 is not necessary. Although two joints are shown in FIG. 1, one joint may be used, or more than two joints may be used.

Figure 2:
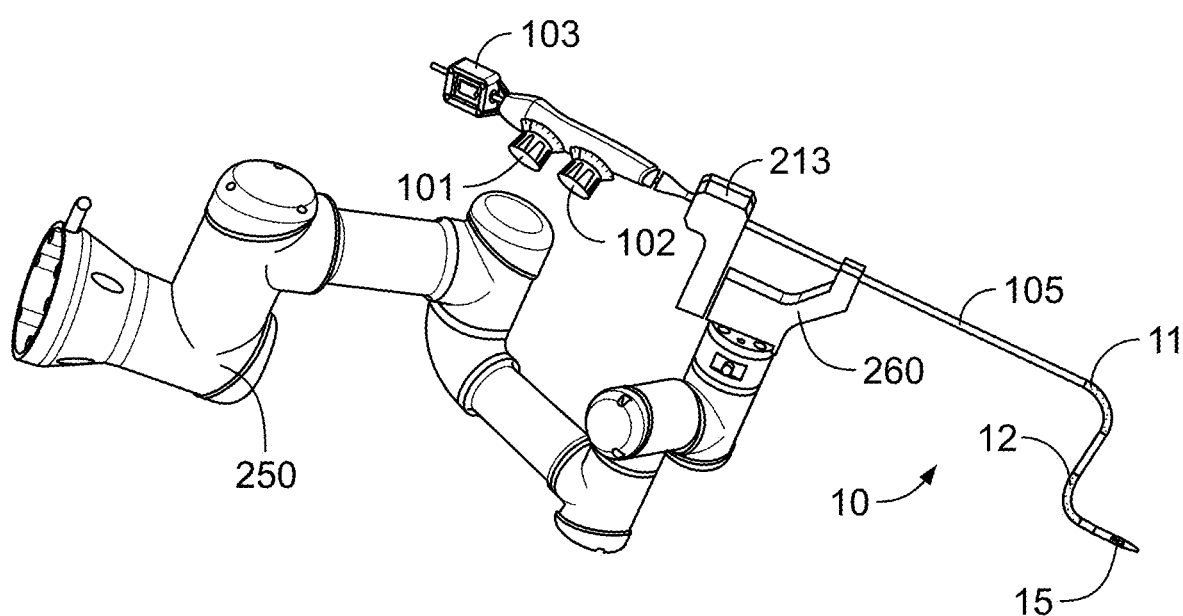
FIG. 2 is a schematic diagram of a multi-jointed robotic arm having a sensorized guide holding an articulated surgical instrument, according to an embodiment of the present invention.

Surgical instrument 10 may be inserted directly into the patient or into a cannula or sensorized guide attached to a robotic arm. Reference is now made to FIG. 2, which is a schematic diagram of a multi-jointed robotic arm 250 having a sensorized guide 260 holding an articulated surgical instrument such as surgical instrument 10, according to an embodiment of the present invention. Details of a robotic arm assembly such as robotic arm 250 and/or sensorized guide 260 are disclosed in U.S. Pat. App. Nos. 62/572,986, 62/627,565, and 62/630,612, and U.S. patent application Ser. Nos. 16/160,575 and 16/275,313, the entireties of which are hereby incorporated by reference. Sensorized guide 260 may include a sensor 213 that tracks the translation and/or rotation of instrument 10. When the three-dimensional position and orientation of the robotic arm assembly and sensorized guide (or other end-effector) are registered to a navigation system that can control the robotic arm assembly, and surgical instrument 10 is rigidly connected to the robot end-effector, then the position and orientation of tip 15 can be calculated with respect to the robotic arm assembly, sensor 213, sensor 103 (if also used), and the readings from dials 101 and 102. Such a navigation system and related method for determining surgical procedure access are described in the above-referenced U.S. Pat. App. No. 62/630,612 and Ser. No. 16/275,313. Those disclosures also reference the use of articulated instruments, such as surgical instrument 10.

Figure 3A:
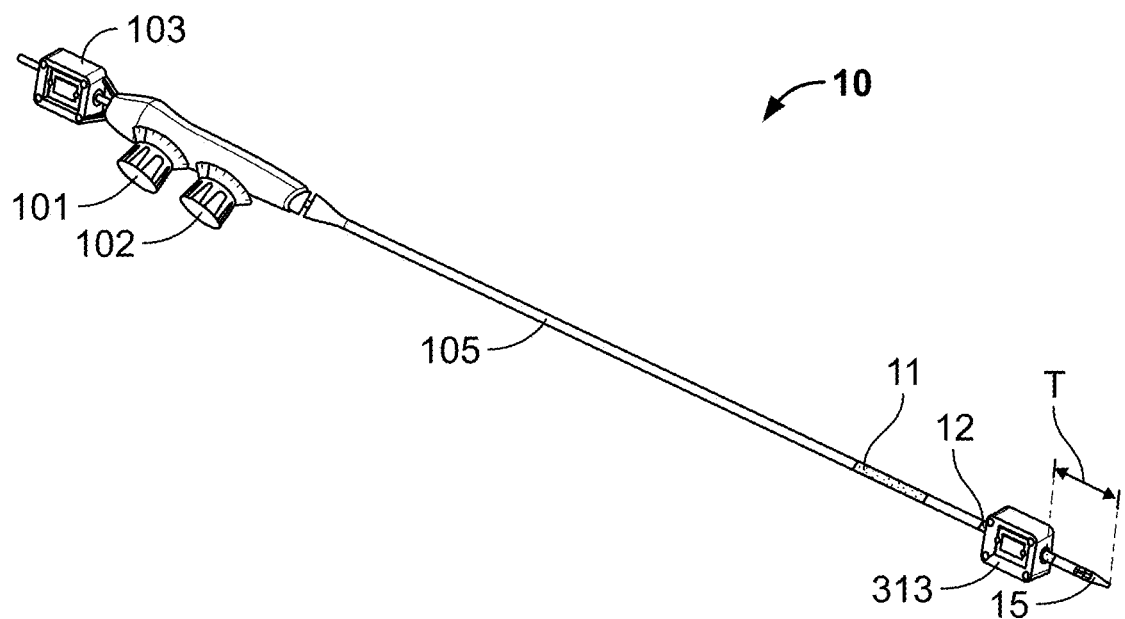
FIGS. 3A-3D are schematic diagrams showing how the articulated surgical instrument of FIG. 1 may be used, according to an embodiment of the present invention.
Figure 3B:
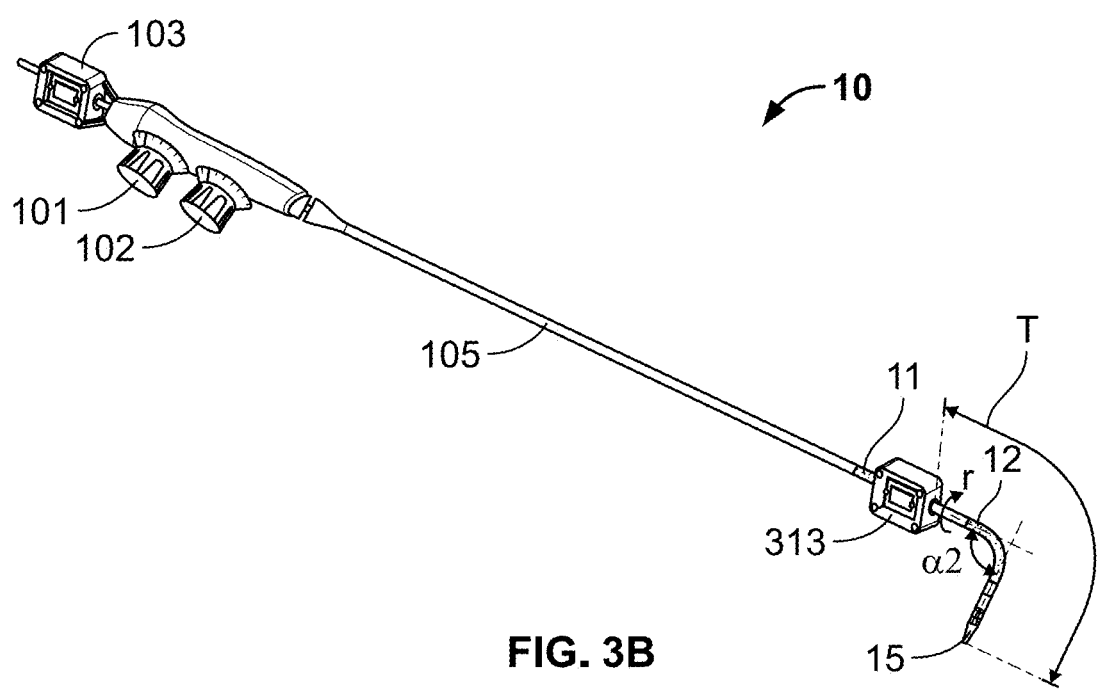

Reference is now made to FIGS. 3A-3D, which are schematic diagrams showing how articulated surgical instrument 10 may be used, according to an embodiment of the present invention. Surgical instrument 10 begins completely straight and is inserted into sensor 313, which is a simplified representation of sensor 213 of FIG. 2. Sensor 313 starts to read an initial instrument translation (travel) T, as shown in FIG. 3A. In FIG. 3B, joint 12 passes through sensor 313 and starts to bend at angle $\alpha_2$, and instrument translation T increases. Knowing angle $\alpha_2$ from dial 102, instrument translation T of tip 15 from sensor 313, and rotation angle r from sensor 313, the position and orientation of tip 15 may be calculated with respect to sensor 313.

Figure 3C:
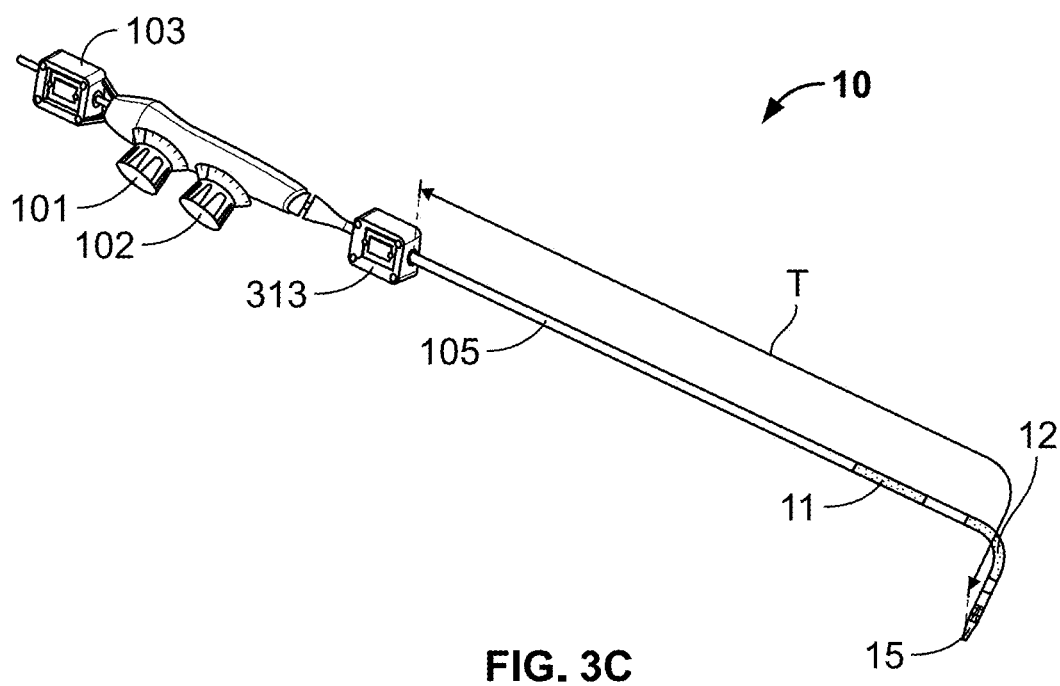
Figure 3D:
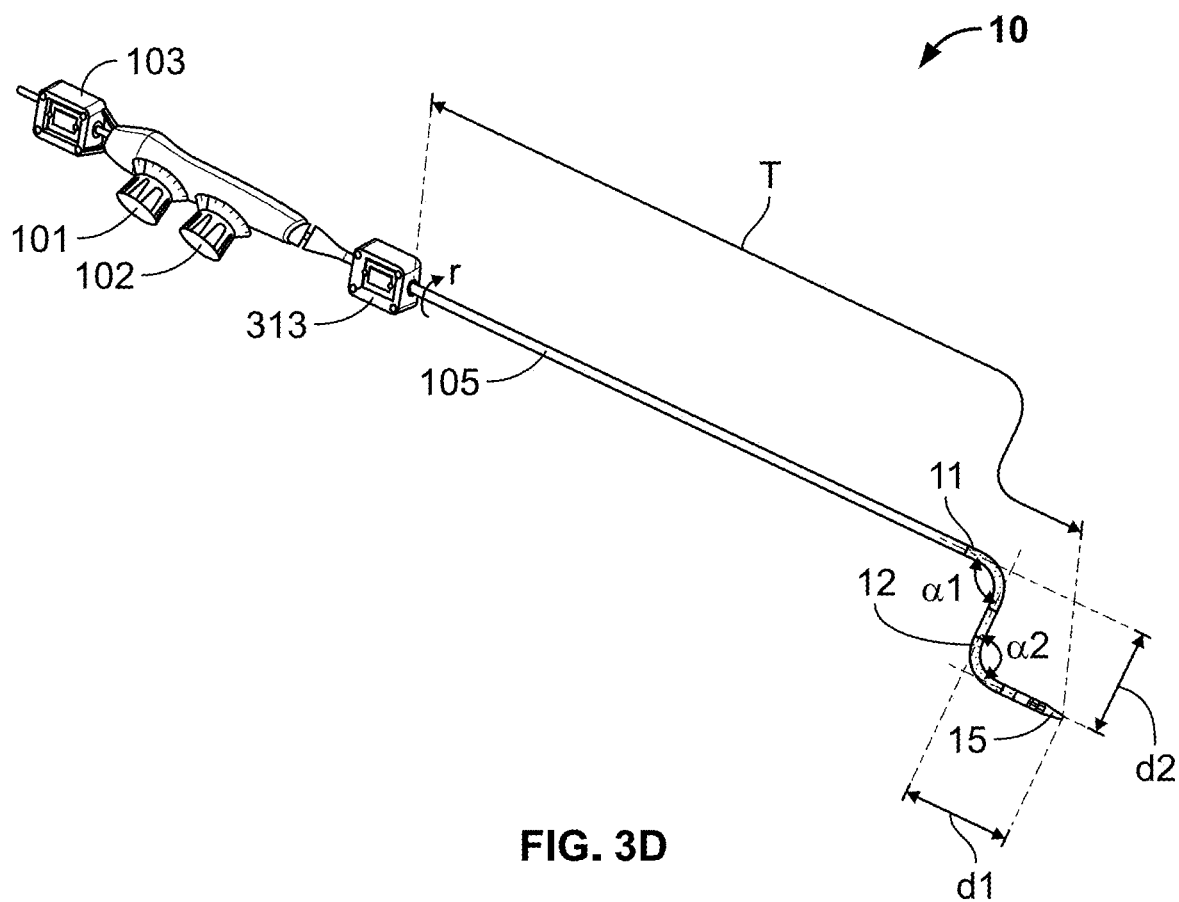

In FIG. 3C, sensor 313 is placed further up surgical instrument 10 to show longer translation T, including a bend in joint 12. In FIG. 3D, the position and orientation of tip 15 with respect to sensor 313 are a function of rotation angle r, translation T, angle $\alpha_1$, and angle $\alpha_2$, where rotation angle r and translation T are read by sensor 313, and angles $\alpha_1$ and $\alpha_2$ are read from dials 101 and 102, respectively. The distances d1 and d2 are defined as follows: d1 is the distance between tip 15 and the center of joint 12; d2 is the distance between the centers of joints 11 and 12.

Figure 4A:
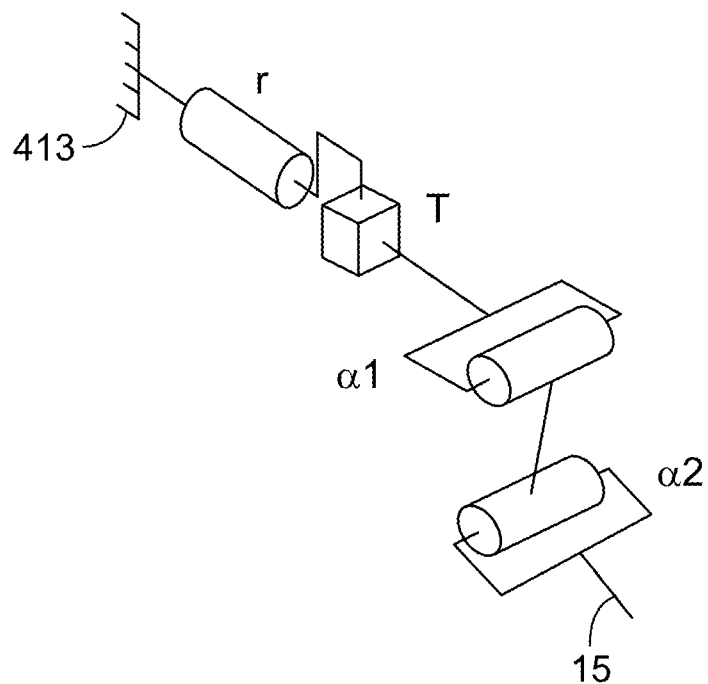
FIG. 4A is a schematic diagram of a kinematic model used to calculate the position and orientation of the tip of an articulated surgical instrument, according to an embodiment of the present invention.

Reference is now made to FIG. 4A, which is a schematic diagram of a kinematic model used to calculate the position and orientation of tip 15, according to an embodiment of the present invention. Ground 413 represents the "ground" of the instrument kinematic chain, which is where the robot connects to the instrument through the mechanics of sensors 213 or 313. This kinematic chain is useful for displaying the structure of the movable chain and is used for analyzing the direct kinematic problem to be solved, as shown below in FIG. 4B. Rotation angle r and translation T from ground 413 and joint bending angles $\alpha_1$ and $\alpha_2$ were described above with respect to sensor 313 in FIGS. 3A-3D. Alternatively, if surgical instrument 10 is held by robotic arm 250, then the position and orientation of tip 15 may be calculated with respect to the location of sensor 213.

Figure 4B:
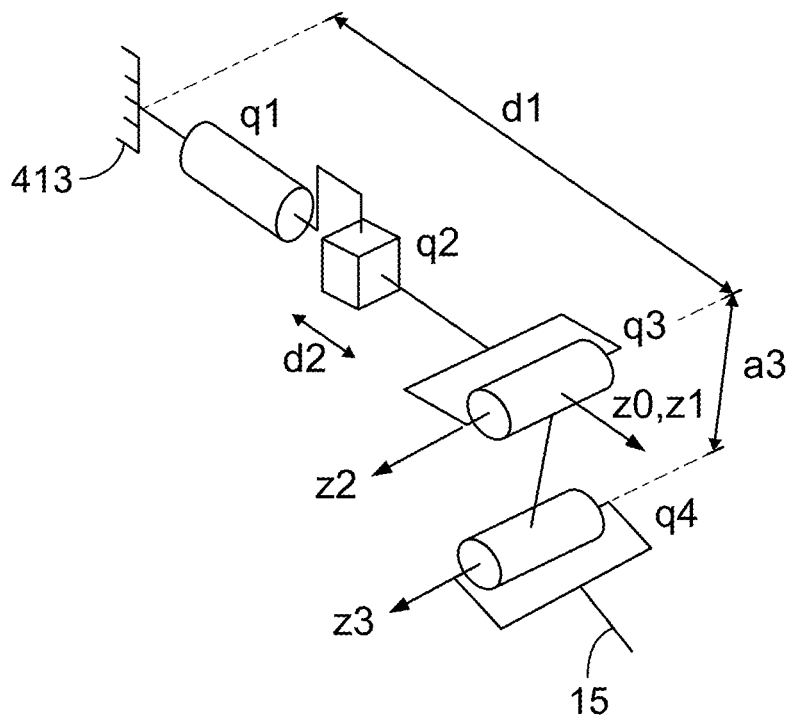
FIG. 4B is a schematic diagram showing how to make a direct kinematic calculation of the position and orientation of the tip of an articulated surgical instrument, according to an embodiment of the present invention.

Reference is now made to FIG. 4B, which is a schematic diagram showing how to make a direct kinematic calculation of the position and orientation of tip 15 with respect to the position and orientation of ground 413 if surgical instrument 10 is held by robotic arm 250. The calculation follows the Denavit-Hartenberg parametrization, which is often used with robotic arms. The Denavit-Hartenberg parameter table for the system in FIG. 4B is as follows:

|  | $a_i$ | $\alpha_i$ | $d_i$ | $\theta_i$ | $\sigma_i$ |
|---|---|---|---|---|---|
| Joint 1 (q1) | 0 | 0 | $d_1$ | $0_1$ | 0 |
| Joint 2 (q2) | 0 | $\frac{\pi}{2}$ | $d_2$ | 0 | 1 |
| Joint 3 (q3) | $a_3$ | 0 | 0 | $\theta_2$ | 0 |
| Joint 4 (q4) | 0 | 0 | 0 | $\theta_3$ | 0 | where, for a joint n:
there is an x-y-z coordinate system, in which:
the z-axis is in the direction of the joint axis;
the x-axis is parallel to the common normal, which is a line perpendicular to both axes of two non-intersecting joint axes (i.e., $x_n = z_n \times z_{n-1}$);
the y-axis follows from the x- and z-axes by choosing the coordinate system to be right-handed;
a is the length of the common normal, which, assuming a revolute joint, is the radius about the previous z-axis;
$\alpha$ is the angle about the common normal, from the previous z-axis to the new z-axis;
d is the offset along the previous z-axis to the common normal. If there is no unique common normal (parallel z-axes), then d is a free parameter;
$\theta$ is the angle about the previous z-axis, from the previous x-axis to the new x-axis; and
$\sigma$ is used as discriminator for a joint, where $\sigma = 0$ for a rotating joint and $\sigma = 1$ for a translation joint.
With the convention that
$c_i = \cos \theta_i$
$s_i = \sin \theta_i$
and that q is the vector q=(q1, q2, q3, q4), the homogeneous transformation matrix $$Kinem = $$
$$T_{0,A}(q) = \begin{vmatrix} c_1 c_3 c_4 - c_1 s_3 c_4 & -c_1 c_3 s_4 - c_1 c_4 s_3 & s_1 & a_3 c_1 c_3 \\ c_3 c_4 s_1 - s_1 s_3 s_4 & -c_3 s_1 s_4 - c_4 s_1 s_3 & -c_1 & a_3 c_3 s_1 \\ c_3 s_4 + c_4 s_3 & c_3 c_4 - s_3 s_4 & 0 & d_1 + d_2 + a_3 s_3 \\ 0 & 0 & 0 & 1 \end{vmatrix}$$

Calling $T_{b,0}$ the transformation between the coordinate system placed on the robot end-effector at ground 413 (which depends on the assembly of the device on the robot) and $T_{4,e}$ the transformation between joint q4 and tip 15 (which depends on the assembly of the tip on surgical instrument 10), the function that calculates position and orientation of tip 15 with respect to the robot end-effector at ground 413 is the matrix product:

$$T_{b,e} = T_{b,0} T_{0,A} T_{4,e}$$

Some benefits of this invention are to provide more accuracy in positioning and orientation of the tip of a surgical instrument and to be able to accurately direct the tip using robotic surgery. When used with a mapping program, the program may be able to control the instrument to avoid obstacles such as organs, bones, and blood vessels.

Aspects of the present invention may be embodied in the form of an apparatus or a system or a method. The above discussion is meant to illustrate the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. An apparatus for use in surgery, comprising:
a sensorized surgical guide comprising a first arm and a second arm, each of the first arm and the second arm having an opening therethrough;
an articulated instrument held by being inserted through the opening of the first arm and the opening of the second arm of the sensorized surgical guide, wherein the articulated instrument has a sleeve and a tip and at least a first joint therebetween capable of bending, the tip passing through the first arm and the second arm as the articulated instrument is inserted through the opening of the first arm and the opening of the second arm;
a sensorized control, at an opposite end portion of the articulated instrument relative to the tip, to change a bending angle of the first joint based on an amount of movement of the sensorized control;
a first sensor tracking the amount of movement of the sensorized control to determine the bending angle of the first joint; and
a second sensor, in the first arm or the second arm of the sensorized surgical guide, measuring translation of the articulated instrument, as the articulated instrument is inserted through the opening of the first arm and the opening of the second arm, to determine, in conjunction with the first sensor, a position of the tip of the articulated instrument,
wherein the sensorized surgical guide is generally U-shaped.

2. The apparatus of claim 1, wherein the sensorized surgical guide is attached to an end of a robotic arm.

3. The apparatus of claim 1, wherein the articulated instrument is rotatable and the sensorized surgical guide measures an amount of rotation of the articulated instrument to determine a position of the tip of the articulated instrument.

4. The apparatus of claim 1, wherein the articulated instrument has a second joint capable of bending between the sleeve of the articulated instrument and the tip of the articulated instrument, wherein the first joint and the second joint have a sleeve portion therebetween.

5. The apparatus of claim 1, wherein the sensorized surgical guide comprises a proximal portion formed with the first arm and a distal portion formed with the second arm, the proximal portion and the distal portion being adapted to be attached together.

6. The apparatus of claim 5, wherein one of the proximal portion and the distal portion is adapted to be in communication with an end portion of a robotic arm.

* * * * *